(12) United States Patent
Lee

(10) Patent No.: US 12,053,355 B2
(45) Date of Patent: Aug. 6, 2024

(54) WOUND DRESSING WITH RE-PEELABLE LID COVER AND LID ABSORBENT PAD

(71) Applicant: Keun Cheol Lee, Busan (KR)

(72) Inventor: Keun Cheol Lee, Busan (KR)

( * ) Notice: Subject to any disclaimer, the term of this patent is extended or adjusted under 35 U.S.C. 154(b) by 401 days.

(21) Appl. No.: 17/608,740

(22) PCT Filed: Dec. 13, 2019

(86) PCT No.: PCT/KR2019/017752
§ 371 (c)(1),
(2) Date: Nov. 3, 2021

(87) PCT Pub. No.: WO2020/226254
PCT Pub. Date: Nov. 12, 2020

(65) Prior Publication Data
US 2022/0313494 A1 Oct. 6, 2022

(30) Foreign Application Priority Data

May 9, 2019 (KR) .................. 10-2019-0054476

(51) Int. Cl.
*A61F 13/00* (2024.01)
*A61F 13/0203* (2024.01)
*A61F 13/0246* (2024.01)

(52) U.S. Cl.
CPC .... *A61F 13/0213* (2013.01); *A61F 13/00063* (2013.01); *A61F 13/0253* (2013.01);
(Continued)

(58) Field of Classification Search
CPC ............ A61F 13/00; A61F 2013/00553; A61F 2013/00557; A61F 2013/0057; A61F 2013/00702; A61F 2013/00748; A61F 2013/00795; A61F 2013/00817; A61F 2013/00821; A61F 13/01–0273;
(Continued)

(56) References Cited

U.S. PATENT DOCUMENTS

| 4,399,816 A | 8/1983 | Spangler |
| 4,470,410 A | 9/1984 | Elliott |

(Continued)

FOREIGN PATENT DOCUMENTS

| CN | 102274574 A | 12/2011 |
| CN | 202136487 U | 2/2012 |

(Continued)

OTHER PUBLICATIONS

English Specification of CN102274574A.
(Continued)

*Primary Examiner* — Kim M Lewis
(74) *Attorney, Agent, or Firm* — ANTONIO HA & U.S. PATENT, LLC

(57) ABSTRACT

The present invention relates to an improved wound dressing member, characterized in that the improved wound dressing member is a laminate comprising: a main body having an opening formed in the central portion thereof, wherein the opening is operable and closable by means of a cover; a cover sheet laminated on top of the main body; a release paper laminated below the main body; and the cover sheet capable of opening or closing the opening by being form-fitted into the opening.

6 Claims, 6 Drawing Sheets

(52) U.S. Cl.
CPC ............ *A61F 2013/0057* (2013.01); *A61F 2013/00702* (2013.01); *A61F 2013/00982* (2013.01)

(58) Field of Classification Search
CPC ...... A61F 2013/00089–00982; A61F 13/0213; A61F 13/0006; A61F 13/0253
See application file for complete search history.

(56) References Cited

U.S. PATENT DOCUMENTS

| | | | | |
|---|---|---|---|---|
| 5,086,763 | A | * | 2/1992 | Hathman ............ A61F 13/0206 602/42 |
| 5,556,375 | A | | 9/1996 | Ewall |
| 5,562,107 | A | * | 10/1996 | Lavender ............. A61F 15/008 602/41 |
| 5,603,946 | A | * | 2/1997 | Constantine .......... A61F 13/025 424/443 |
| 5,607,388 | A | * | 3/1997 | Ewall ................... A61F 13/023 604/304 |
| 5,702,356 | A | * | 12/1997 | Hathman ............ A61F 13/0206 602/41 |
| 6,992,232 | B1 | * | 1/2006 | Kemeny ............... A61F 15/005 602/41 |
| 7,118,545 | B2 | * | 10/2006 | Boyde ................. A61F 13/0226 602/53 |
| 9,549,736 | B2 | * | 1/2017 | Barcroft ................. A61B 17/08 |
| 11,000,419 | B2 | * | 5/2021 | Clippert .................. A61L 15/26 |
| 2007/0043316 | A1 | | 2/2007 | Carlson et al. |
| 2009/0287133 | A1 | * | 11/2009 | LaGreca, Sr. ...... A61F 13/00063 601/84 |
| 2015/0173758 | A1 | | 6/2015 | Barcroft et al. |
| 2017/0202711 | A1 | * | 7/2017 | Cernasov ........... A61F 13/00055 |
| 2018/0153744 | A1 | * | 6/2018 | Al-Heraibi ............ A61F 13/023 |
| 2018/0250169 | A1 | * | 9/2018 | Stanford ........... A61F 13/00059 |
| 2019/0321234 | A1 | * | 10/2019 | Yeung ................. A61F 13/0233 |
| 2022/0151834 | A1 | * | 5/2022 | Simmons ................ A61F 13/05 |

FOREIGN PATENT DOCUMENTS

| | | | |
|---|---|---|---|
| CN | 102379775 | A | 3/2012 |
| CN | 107073163 | A | 8/2017 |
| CN | 208582595 | U | 3/2019 |
| JP | H02-74252 | A | 3/1990 |
| JP | H08-033674 | A | 2/1996 |
| JP | 2001-511396 | A | 8/2001 |
| JP | 2003-033383 | A | 2/2003 |
| JP | 2006-311913 | A | 2/2003 |
| JP | 2008-054818 | A | 3/2008 |
| JP | 3210850 | U | * 6/2017 |
| JP | 2017-528231 | A | 9/2017 |
| KR | 10-2003-0072418 | | 9/2003 |
| KR | 20-2012-0003231 | | 5/2012 |
| KR | 10-1426740 | | 8/2014 |
| KR | 10-2016-0118877 | | 10/2016 |
| KR | 10-2017-0005574 | | 1/2017 |
| KR | 10-2017-0072187 | | 6/2017 |
| NO | 176307 | B | * 12/1994 ......... A61F 13/0203 |
| WO | WO-9005558 | A | * 5/1990 ............ A61K 9/703 |
| WO | WO-2004041064 | A2 | * 5/2004 ............ A61F 13/02 |
| WO | WO-2016100089 | A1 | * 6/2016 ....... A61F 13/00017 |
| WO | WO-2017220404 | A1 | * 12/2017 ....... A61F 13/00085 |

OTHER PUBLICATIONS

English Specification of CN208582595U.
English Specification of JPH08-033674A.
English Specification of JP2001-511396A.
English Specification of JP2003-033383A.
English Specification of JP2006-311913A.
English Specification of JP2008-054818A.
English Specification of 10-1426740.
English Specification of 10-2016-0118877.
English Specification of 10-2017-0072187.
English Specification of CN102379775A.
English Specification of CN107073163A.
English Specification of CN202136487U.
English Specification of 10-2003-0072418.
English Specification of 10-2017-0005574.
English Specification of 20-2012-0003231.
English Specification of JPH02-74252A.
English Specification of JP2017-528231A.

* cited by examiner

[FIG. 1]
PRIOR ART
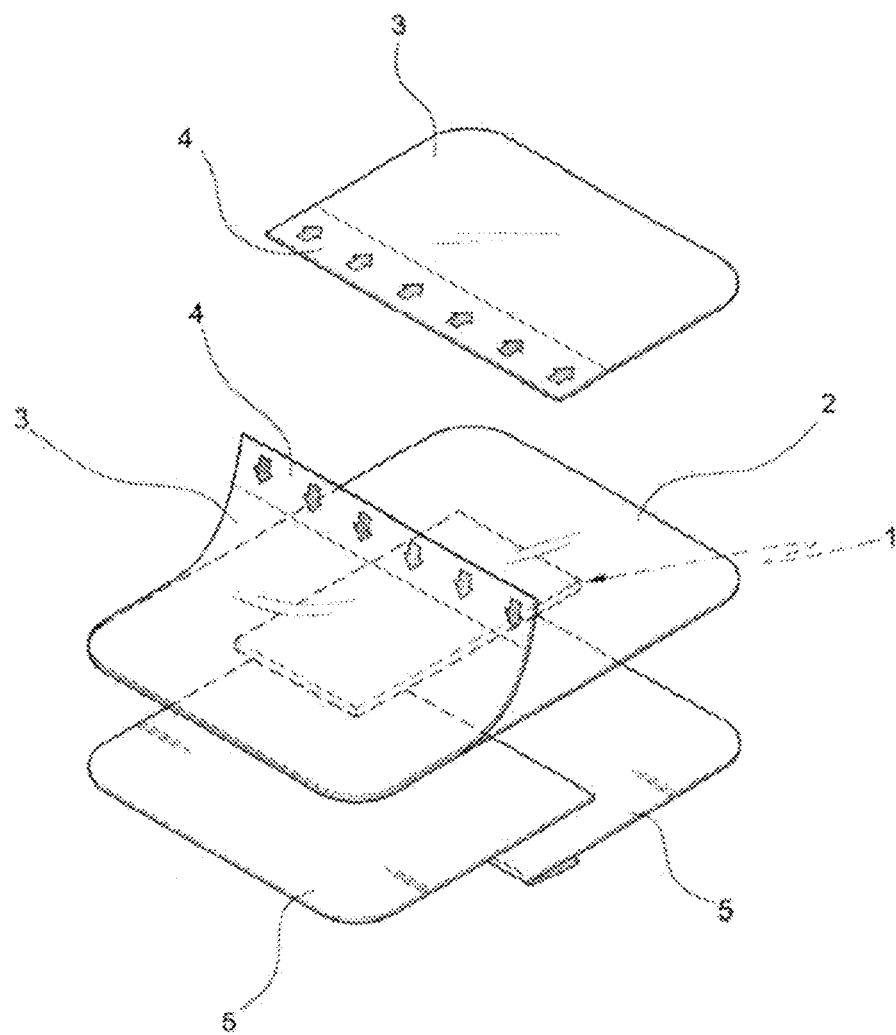

[FIG. 2]
PRIOR ART
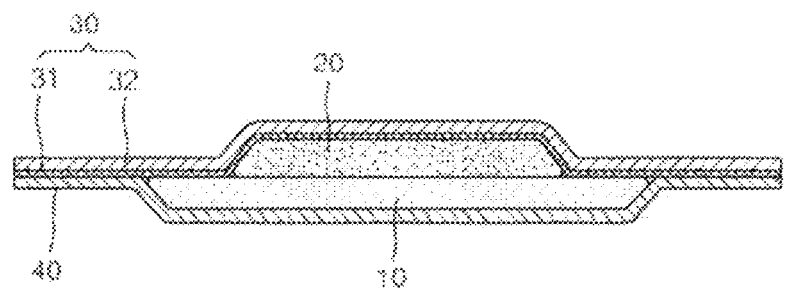
[FIG. 3]
PRIOR ART
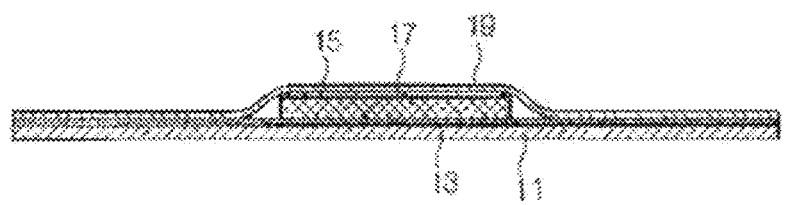

[FIG. 4]
PRIOR ART
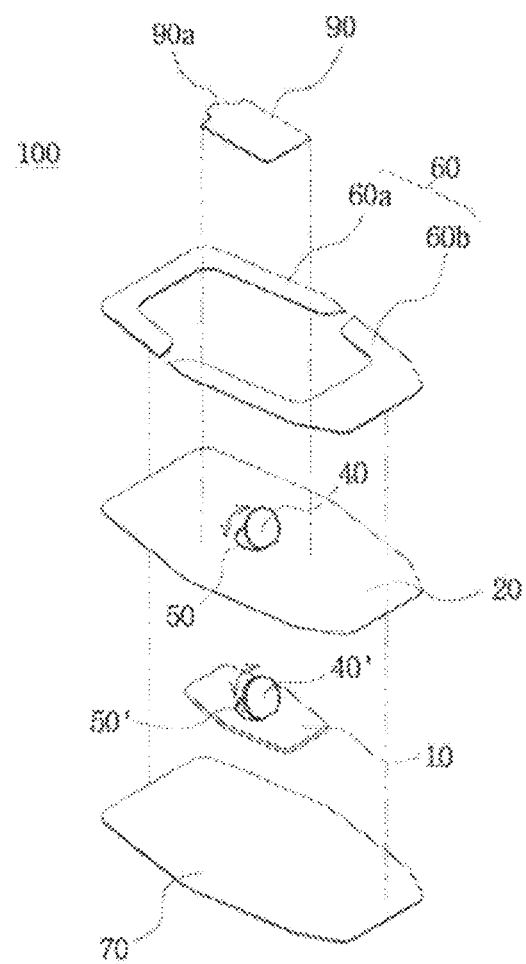

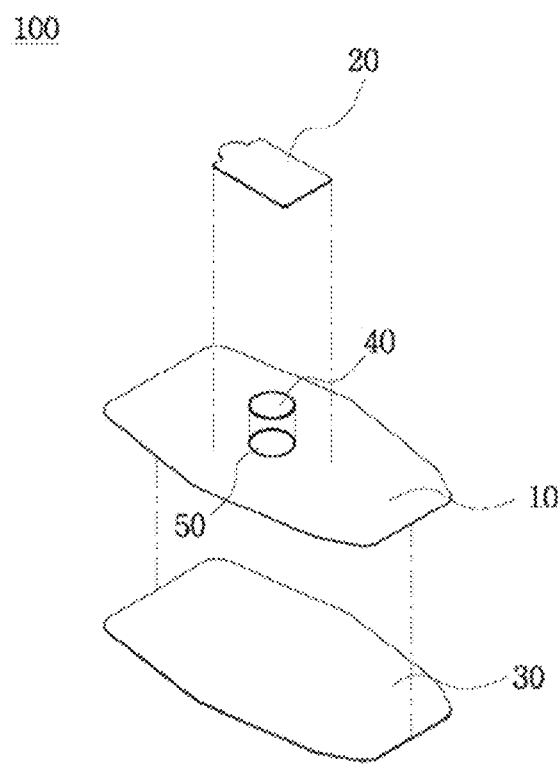
[FIG. 5]

[FIG. 6]
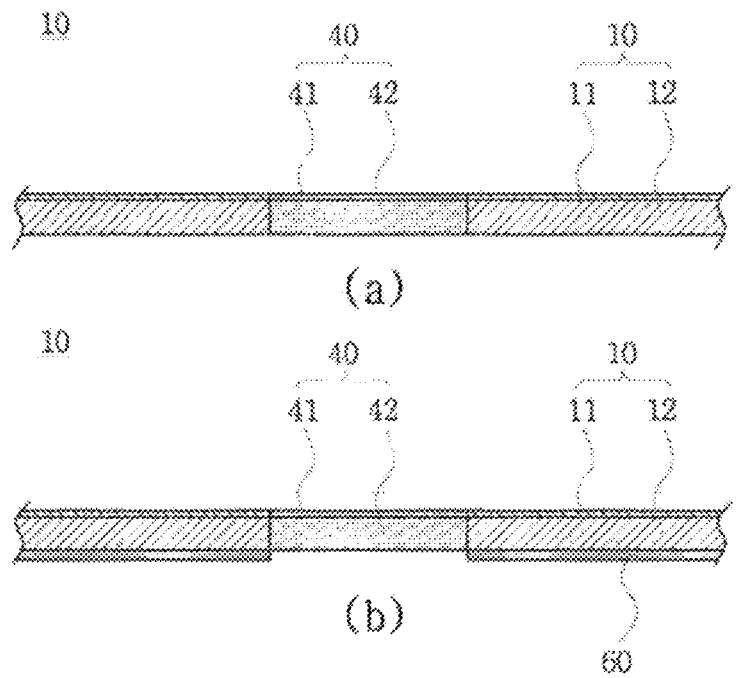
[FIG. 7]
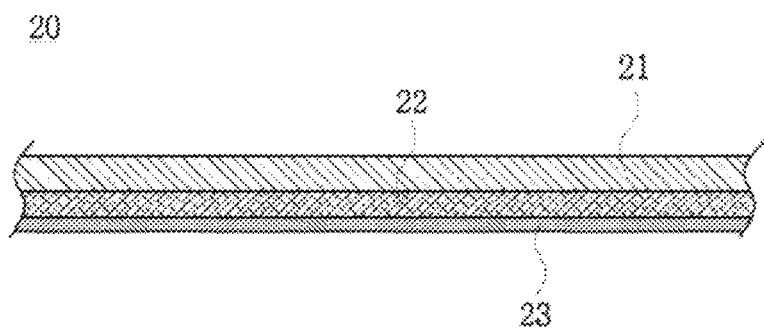

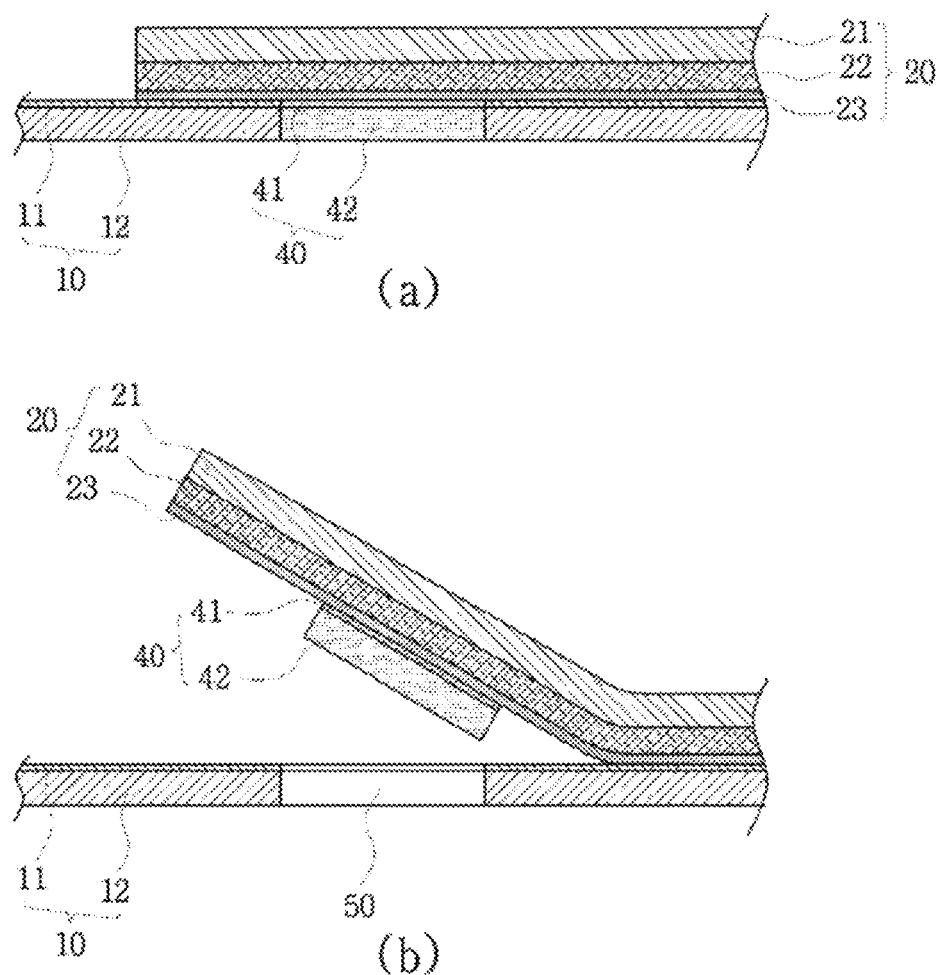
[FIG. 8]

WOUND DRESSING WITH RE-PEELABLE LID COVER AND LID ABSORBENT PAD

TECHNICAL FIELD

The present invention relates to a modified member for dressing a wound, and more particularly to a modified member for dressing a wound, which is configured such that it can be simply attached to a wound area of a patient's body, enables to easily administer a treatment ointment for external application for rapid healing of the wound area along with monitoring of the wound area, a therapeutic agent or drug, or the like anytime, can alleviate a pain occurring during removal of the modified member from the affected part of the patient with the aid of a smooth silicone pressure-sensitive adhesive unlike a conventional general adhesive tape, and can increase the patient's satisfaction with the use of the modified member and the convenience of medical staff as a secondary dressing procedure is unnecessary by eliminating the necessity for the use of an adhesive plaster or tape.

BACKGROUND ART

'Wound' on the skin of the body refers to a state where the normal structure of body tissue is damaged by an externally applied force. Thus, it is known that wound healing is promoted only when the wound is in light damp or occluded conditions. In the case where excessive exudate remains in the wound area, a lower portion of a member for dressing a wound is swollen by the exudate, which makes the wound area invisible. In addition, when the wound dressing member absorbs the exudate completely to remove the exudate, there occurs a problem in that the wound area becomes dry, and thus the progress of the wound healing is retarded.

Thus, in an attempt to solve the above-mentioned problems, various technologies such as employing a member coated with hydrogel to maintain the wound area in a wet state or employing a member capable of properly absorbing exudate are developed and their related patent applications are filed in Korea and foreign countries.

Korean Patent Laid-Open Publication No. 10-2017-0005574 (laid-open on Jan. 16, 2017) is directed to a bandage for wound dressing. As shown in FIG. 1, the bandage includes a structure in which an atelo-collagen sponge (not shown) is attached to a portion of a hydrogel 1 and a transparent pressure-sensitive adhesive film 2 for fixing the hydrogel 1 to a wound area and Korean Utility Model Laid-Open Publication No. 20-2012-0003231 (laid-open on May 9, 2012) is directed to a wound dressing material using carboxymethylcellulose fiber. As shown in FIG. 2, the wound dressing material includes: a wound contact layer 10 having a liquid permeable sheet for allowing exudate generated from a wound to permeate therethrough; an absorbent layer 20 containing carboxymethylcellulose fiber; and a support layer 30 including a synthetic polymer film on one surface of which a pressure-sensitive adhesive is coated to allow the wound contact layer 10 to come into close contact with the skin therethrough. Korean Patent Laid-Open Publication No. 10-2003-0072418 (laid-open on Sep. 15, 2003) is directed to a wound dressing on which an ointment type dressing agent is applied. As shown in FIG. 3, the wound dressing includes a structure in which a pressure-sensitive adhesive layer 13 is adhered to a base 11 to allow the wound dressing to be attached to the skin around a wound area therethrough, and a dressing substrate 15 is adhered to the pressure-sensitive adhesive layer 13. As mentioned above, various wound dressing members are known in the art.

However, the above-mentioned conventional wound dressing members have similarities in that it employs a drug capable of treating a wound while maintaining a wound area in a wet state, but entail problems in that when a medical staff desires to observe the wound area of a patient with naked eyes, he or she suffers from inconvenience of having to completely remove the wound dressing members from the wound area. In addition, the conventional wound dressing members involve problems in that pain may be caused to the wound area of the patient during removal of the wound dressing members from the wound area, and in that when it is desired to reuse the wound dressing members, the affected part of the patient may be contaminated from external bacteria.

In the meantime, the present applicant has developed a member for preventing bedsores, which has a structure as shown in FIG. 4, and has been granted a patent for the member for preventing bedsores as disclosed in Korean Patent No. 10-1923986 (issued on Feb. 22, 2019). In addition, the present applicant has improved the member for preventing bedsores of Korean Patent No. 10-1923986 (issued on Feb. 22, 2019), and then has developed a member for dressing a wound that can solve problems occurring in the bandage for wound dressing as disclosed in the above-mentioned Korean Patent Laid-Open Publication No. 10-2017-0005574 (laid-open on Jan. 16, 2017), the wound dressing material using carboxymethylcellulose fiber as disclosed in the above-mentioned Korean Utility Model Laid-Open Publication No. 20-2012-0003231 (laid-open on May 9, 2012), and the wound dressing material on which an ointment type dressing agent is applied as disclosed in the above-mentioned Korean Patent Laid-Open Publication No. 10-2003-0072418 (laid-open on Sep. 15, 2003), thereby completing the present invention.

DISCLOSURE OF INVENTION

Technical Problem

Accordingly, the present invention has been made in order to solve the above-described problems occurring in the prior art, and it is an object of the present invention is to provide a modified member for dressing a wound in which it includes a lid cover disposed on an upper outer surface thereof and having an area larger than that of a lid, and a nonwoven fabric of a release material layer of the lid cover is adhered to a protective layer of a synthetic resin film material, which is an upper layer of the main body, by means of a pressure-sensitive adhesive layer, so that attachment and detachment between the protective layer and the release material layer is facilitated by the synthetic resin film and the nonwoven fabric that are heterogeneous materials to allow the lid to be easily opened or closed relative to the opening.

Another object of the present invention is to provide a modified member for dressing a wound in which a silicone pressure-sensitive adhesive layer is formed on the remaining underside surface of the main body other than the opening corresponding to a position of the wound area, so that when a wound occurs on the skin, the modified member can be easily attached to the wound area, and when the modified member is detached from the wound area, a pain occurring during removal of the modified member from the affected part can be alleviated and adhesive plaster allergy can be avoided with the aid of a smooth silicone pressure-sensitive adhesive.

Still another object of the present invention is to provide a modified member for dressing a wound in which when the pad layer of the lid is contaminated due to exudate or hemorrhage generated from the skin or wounds, the lid can be easily replaced with a new one, in which the lid can be easily opened or closed relative to the opening anytime to enable to check a wound healing state of the patient with naked eyes, and in which a treatment ointment for external application, therapeutic agent or drug or the like can be easily administered to the wound area so that the wound healing is promoted to reduce the sickbed life period of the patient, leading to a reduction in the medical expenditure.

Yet another object of the present invention is to provide a modified member for dressing a wound in which a pad layer of a synthetic resin film formed in a sheet type from synthetic resin foam and hydrocolloid or hydrogel is used in an aseptic state or is used by impregnating the synthetic resin foam with hydrocolloid or hydrogel, so that a wound area is prevented from being dried and is maintained in a wet state, thereby promoting wound healing.

Technical Solution

To achieve the above objects, the present invention provides a modified member for dressing a wound, which includes: a main body 10 having an opening 50 formed at a central portion thereof so as to be openable/closable; a lid cover 20 stackedly disposed on a top surface of the main body 10; a release paper 30 stackedly disposed on an underside surface of the main body (10); and a lid 40 disposed at the opening 50 and formed in a shape of corresponding to the shape of the opening 50 to enable the lid 40 to open or close the opening 50 by press-fit engagement, whereby the main body, the lid cover, the release paper 30, and the lid 40 form a stacked body.

In addition, the lid cover 20 may include a structure in which a cover layer 21, a release material layer 22, and a pressure-sensitive adhesive layer 23 are stacked downwards in order, the lid cover 20 having an area lager than that of the lid 40. The lid cover 20 may include a structure in which the release material layer 22 is adhered to a protective layer 11 that is an upper layer of the main body 10 by means of the pressure-sensitive adhesive layer 23.

Further, the lid 40 may include a stacked body composed of a protective layer 41 and a pad layer 42. The main body 10 may include either a stacked body composed of a protective layer 11 and a pad layer 12, or a stacked body composed of a protective layer 11, a pad layer 12, and a silicone pressure-sensitive adhesive layer 60. The pad layer 12 may be obtained by impregnating the synthetic resin foam with hydrocolloid or hydrogel.

Advantageous Effects

The modified member for dressing a wound according to the present invention has effects in that it includes a lid cover disposed on an upper outer surface thereof and having an area larger than that of a lid, and a nonwoven fabric of a release material layer of the lid cover is adhered to a protective layer of a synthetic resin film material, which is an upper layer of the main body, by means of a pressure-sensitive adhesive layer, so that attachment and detachment between the protective layer and the release material layer is facilitated by the synthetic resin film and the nonwoven fabric that are heterogeneous materials to allow the lid to be easily opened or closed relative to the opening.

In addition, the modified member for dressing a wound according to the present invention has effects in that a silicone pressure-sensitive adhesive layer is formed on the remaining underside surface of the main body other than the opening corresponding to a position of the wound area, so that when a wound occurs on the skin, the modified member can be easily attached to the wound area, and when the modified member is detached from the wound area, a pain occurring during removal of the modified member from the affected part can be alleviated and adhesive plaster allergy can be avoided with the aid of a smooth silicone pressure-sensitive adhesive.

Further, the modified member for dressing a wound according to the present invention has effects in that when the pad layer 42 of the lid 40 is contaminated due to exudate or hemorrhage generated from the skin or wounds, the lid can be easily replaced with a new one, in that the lid can be easily opened or closed relative to the opening anytime to enable to check a wound healing state of the patient with naked eyes, and in that a treatment ointment for external application, therapeutic agent or drug or the like can be easily administered to the wound area so that the wound healing is promoted to reduce the sickbed life period of the patient, leading to a reduction in the medical expenditure.

Besides, the modified member for dressing a wound according to the present invention has effects in that a pad layer of a synthetic resin film formed in a sheet type from synthetic resin foam and hydrocolloid or hydrogel is used in an aseptic state or is used by impregnating the synthetic resin foam with hydrocolloid or hydrogel, so that a wound area is prevented from being dried and is maintained in a wet state, thereby promoting wound healing.

Furthermore, the modified member for dressing a wound according to the present invention has effects in that a secondary dressing procedure is unnecessary so that the patient's satisfaction with the use of the modified member and the convenience of medical staff can be increased, unlike a conventional wound dressing member in which the secondary dressing procedure is necessary to fix the wound dressing member to an affected part of a patient during the use of the wound dressing member.

BRIEF DESCRIPTION OF THE DRAWINGS

FIGS. 1 to 3 are perspective and cross-sectional views showing a member for dressing a wound according to the prior art;

FIG. 4 is an exploded perspective view showing a member for preventing bedsore as disclosed in Korean Patent No. 10-1923986 (issued on Feb. 22, 2019)) for which the present applicant has been granted a patent;

FIG. 5 is an exploded perspective view showing a modified member for dressing a wound according to a preferred embodiment of the present invention;

FIGS. 6(a) and 6(b) are longitudinal cross-sectional views showing a main body of a modified member for dressing a wound according to a preferred embodiment of the present invention;

FIG. 7 is a longitudinal cross-sectional view showing a lid cover of a modified member for dressing a wound according to a preferred embodiment of the present invention; and FIGS. 8(a) and 8(b) are longitudinal cross-sectional views showing a state in which an opening is opened and closed by a lid of a modified member for dressing a wound according to a preferred embodiment of the present invention.

BEST MODE FOR CARRYING OUT THE INVENTION

Hereinafter, a preferred embodiment of the present invention will be described in further detail with reference to the accompanying drawings. In FIGS. 5 to 8, elements performing the same function are denoted by identical reference numerals. In the meantime, in the detailed description and the accompanying drawings, illustration and explanation on the detailed technical construction and operation of elements, which have no direct connection with the technical features of the present invention, will be omitted, and only the technical constructions directly related with the present invention will be briefly illustrated and explained.

For reference, in terms used herein, when describing each layer of a stacked body of the modified member 100, the term 'inner surface' refers to a face of the side of the modified member, which comes into direct contact with a patient's skin, and the term 'outer surface' refers to a face opposed to the 'inner surface'.

Referring to FIGS. 5 to 8, a modified member 100 for dressing a wound according to the present invention includes: a main body 10 having an opening 50 formed at a central portion thereof so as to be openable/closable; a lid cover 20 stackedly disposed on a top surface of the main body 10; a release paper 30 stackedly disposed on an underside surface of the main body 10; and a lid 40 disposed at the opening 50 and formed in a shape of corresponding to the shape of the opening 50 to enable the lid 40 to open or close the opening 50 by press-fit engagement, whereby the main body 10, the lid cover 20, the release paper 30, and the lid 40 form a stacked body.

Hereinafter, a stacked structure of the respective layers of the modified member 100 for dressing a wound according to the present invention will be described in detail.

The main body 10 is a member having a face that comes into direct contact with a patient's skin, and has a structure in which it has the opening 50 formed at the central portion thereof so that the opening 50 can be opened or closed by the lid 40. The main body 10 includes a stacked body structure composed of a protective layer 11 and a pad layer 12 as shown in FIG. 6(a), or a stacked body structure composed of a protective layer 11, a pad layer 12, and a silicone pressure-sensitive adhesive layer 60 as shown in FIG. 6(b).

The protective layer 11 is a layer formed on an upper portion of the main body 10. A material used for the protective layer 11 may be selected from among various synthetic resin materials such as polyurethane (PU), polyethylene (PE), and polypropylene (PP), but in addition to the limited examples of the material, any material may be used without limitation as long as it is a material that has the physical properties equivalent to those of the above-enumerated materials and is harmless to the human body.

The pad layer 12 is a layer formed on a lower portion of the main body 10. Preferably, a material used for the pad layer 12 is selected from among various synthetic resin materials or film materials such as polyurethane (PU), polyethylene (PE), and polypropylene (PP). In addition, the pad layer 12 that can be used in the present invention may be obtained by impregnating synthetic resin foam with hydrocolloid or hydrogel, or may be obtained in the form of a synthetic resin film formed in a sheet type from synthetic resin foam and hydrocolloid or hydrogel.

Hydrocolloid (hydrophilic colloid) that can be used in the present invention may be one or more selected from among collagen, hydroxyethylcellulose, methylcellulose, ethylcellulose, and carboxymethylcellulose sodium. In addition to the limited examples of the hydrocolloid, any material may be used without limitation as long as it is a material that has the physical properties equivalent to those of the above-enumerated materials.

As such, hydrocolloid or hydrogel that is used in the present invention acts to prevent a wound area from being dried and maintain the wound area in a wet state, and thus has an effect of promoting wound healing. The pad layer of a synthetic resin film formed in the sheet type is used in an aseptic state or acts to impart a wound healing effect by impregnating the synthetic resin foam with hydrocolloid or hydrogel.

The silicone pressure-sensitive adhesive layer 60 is formed on the remaining underside surface of the main body 10 other than the opening 50 corresponding to a position of the wound area, so that when a wound occurs on the skin, the modified wound dressing member can be easily attached to the wound area, and when the modified wound dressing member is detached from the wound area, adhesive plaster allergy can be avoided and a pain occurring during removal of the modified member from the affected part can be alleviated with the aid of a smooth silicone pressure-sensitive adhesive.

The opening 50 formed at the central portion of the main body 10 has a structure in which it can be opened or closed by press-fit engagement of the lid 40 having a shape corresponding to the shape of the opening. The lid 40 includes a stacked body composed of a protective layer 41 and a pad layer 42 as shown in FIGS. 6 and 8.

A material used for the protective layer 41 and the pad layer 42 of the lid 40 is the same as that used for the protective layer 11 and the pad layer 12 of the main body 10

The lid cover 20 includes a structure in which a cover layer 21, a release material layer 22, and a pressure-sensitive adhesive layer 23 are stacked downwards in order. The lid cover 20 has an area larger than that of the lid 40. The lid cover 20 may include a knob (not shown) formed at a proper portion of one side or both sides thereof to facilitate the opening/closing of the lid 40 relative to the opening 50.

The cover layer 21 is a layer that serves to protect the lid cover 20. A material used for the cover layer 21 is the same as that used for the protective layer 11 of the main body 10.

The release material layer 22 has a structure in which it is integrally bonded to an underside surface of the cover layer 21, and a material used for the release material layer is preferably selected from among a nonwoven fabric, a natural fiber fabric, and a synthetic fiber fabric. In addition to the enumerated release materials, any material may be used without limitation as long as it is a material that has the release properties that it can be easily separated from the synthetic resin film adhered thereto and is harmless to the human body.

The pressure-sensitive adhesive layer 23 is a layer that has a pressure-sensitive adhesive coated on an underside surface of the release material layer 22. The pressure-sensitive adhesive layer 23 is a layer formed to adhere the nonwoven fabric, the natural fiber fabric or the synthetic fiber fabric of the release material layer 22 to the protective layer 11 of a synthetic resin film material of the main body 10. The pressure-sensitive adhesive used in the present invention is preferably a polyurethane-based pressure-sensitive adhesive that is harmless to the human body, but is necessarily not limited thereto. Any pressure-sensitive adhesive may be used without limitation as long as it is a material that has the physical properties equivalent to those of the pressure-sensitive adhesive.

Thus, the modified member 100 for dressing a wound according to the present invention includes the lid cover 20 formed on the upper outer surface thereof and having an area larger than that of the lid 40, and the nonwoven fabric of the release material layer 22 of the lid cover 20 is adhered to the protective layer 11 of a synthetic resin film material, which is an upper layer of the main body 10, by means of the pressure-sensitive adhesive layer 23, so that attachment and detachment between the protective layer 11 and the release material layer 22 is facilitated by the synthetic resin film and the nonwoven fabric that are heterogeneous materials as shown FIGS. 8(a) and 8(b). Thus, the modified wound dressing member 100 of the present invention has an effect in that the lid 40 is easily opened or closed relative to the opening 50 as shown in FIG. 8(b).

The release paper 30 is a layer for protecting the modified member for dressing a wound. In other words, the release paper 30 is a layer that is adhered to and laminated on an underside surface of the main body 10 by means of a pressure-sensitive adhesive harmless to the human body, coated on a surface abutting against the modified wound dressing member. As the release paper 30, a synthetic resin film, a synthetic resin coated paper, a silicone coated paper, a natural fabric, or a synthetic resin fabric which is in an aseptic state may be used.

Further, the release paper 30 may have a pressure-sensitive adhesive coated thereon, if necessary. The pressure-sensitive adhesive used to be coated on the release paper 30 is the same as that used in the pressure-sensitive adhesive layer 23 of the lid cover 20.

As described above, according to the modified member 100 for dressing a wound of the present invention, when the pad layer 42 of the lid 40 is contaminated due to either exudate or hemorrhage generated from the skin or wounds, the lid 40 adhered to the pressure-sensitive adhesive layer 23 of the lid cover 20 is separated from the lid cover 20 and then the lid 40 can be easily replaced with a new aseptic lid 40. In addition, the lid 40 can be easily opened or closed relative to the opening 50 anytime to enable to check a wound healing state of the patient with naked eyes. Further, a treatment ointment for external application, therapeutic agent or drug or the like can be easily administered to the wound area so that the wound healing is promoted to reduce the sickbed life period of the patient, leading to a reduction in the medical expenditure.

Thus, the modified member for dressing a wound according to the present invention makes it unnecessary to perform a secondary dressing procedure so that the patient's satisfaction with the use of the modified member and the convenience of medical staff can be increased, unlike a conventional wound dressing member in which the secondary dressing procedure is necessary to fix the wound dressing member to an affected part of a patient during the use of the wound dressing member.

While the modified member for dressing a wound according to the present invention has been described and illustrated in connection with specific exemplary embodiments with reference to the accompanying drawings, it will be readily appreciated by those skilled in the art that it is merely illustrative of the preferred embodiments of the present invention, and various modifications and changes can be made thereto within the technical spirit and scope of the present invention.

BEST MODE

In a best mode for carrying out the present invention, the present invention provides a modified member for dressing a wound, which includes: a main body 10 having an opening 50 formed at a central portion thereof so as to be openable/closable; a lid cover 20 stackedly disposed on a top surface of the main body 10; a release paper 30 stackedly disposed on an underside surface of the main body 10; and a lid 40 disposed at the opening 50 and formed in a shape of corresponding to the shape of the opening 50 to enable the lid 40 to open or close the opening 50 by press-fit engagement, whereby the main body 10, the lid cover 20, the release paper 30, and the lid 40 form a stacked body.

INDUSTRIAL APPLICABILITY

The modified member for preventing bedsores according to the present invention is expected to be industrially applicable in that it can be simply attached to a wound area of a patient's body, enables to easily administer a treatment ointment for external application for rapid healing of the wound area along with monitoring of the wound area, a therapeutic agent or drug, or the like anytime, can alleviate a pain occurring during removal of the modified member from the affected part of the patient with the aid of a smooth silicone pressure-sensitive adhesive unlike a conventional general adhesive tape, and can increase the patient's satisfaction with the use of the modified member and the convenience of medical staff as a secondary dressing procedure is unnecessary by eliminating the necessity for the use of an adhesive plaster or tape, and in that a secondary dressing procedure is unnecessary so that the patient's satisfaction with the use of the modified member and the convenience of medical staff can be increased, unlike a conventional wound dressing member in which the secondary dressing procedure is necessary to fix the wound dressing member to an affected part of a patient during the use of the wound dressing member.

The invention claimed is:

1. A modified member for dressing a wound, which comprises:
  a main body (10) having an opening (50) formed at a central portion thereof so as to be openable or closable;
  a lid cover (20) stacked on a top surface of the main body (10);
  a release paper (30) stacked on an underside surface of the main body (10); and
  a lid (40) disposed at the opening (50) and formed in a shape corresponding to the shape of the opening (50) to enable the lid (40) to open or close the opening (50) by press-fit engagement,
  whereby the main body (10), the lid cover (20), the release paper (30), and the lid (40) form a stacked body,
  wherein the main body (10) comprises a stacked body composed of a protective layer (11) and a pad layer (12),
  wherein the lid cover (20) comprises a structure in which a cover layer (21), a release material layer (22), and a pressure-sensitive adhesive layer (23) are stacked downwards in order,
  wherein the lid (40) comprises a stacked body composed of a protective layer (41) and a pad layer (42),
  wherein the release material layer (22) of the lid cover (20) has nonwoven fabric, and the protective layer (11) of the main body (10) has synthetic resin film material so that attachment and detachment between the protective layer (11) of the main body (10) and the release material layer (22) of the lid cover (20) is facilitated by the synthetic resin film and the nonwoven fabric that are heterogeneous materials, and wherein a material used for the protective layer (41) of the lid (40) is the same as that used for the protective layer (11) of the main body (10), and a material used for pad layer (42) of the lid (40) is the same as that used for the pad layer (12) of the main body (10).

2. The modified member for dressing a wound according to claim 1, wherein the lid cover (20) have an area larger than that of the lid (40).

3. The modified member for dressing a wound according to claim 1, wherein the lid cover (20) comprises a structure in which the release material layer (22) is adhered to the protective layer (11) that is an upper layer of the main body (10) by means of the pressure-sensitive adhesive layer (23).

4. The modified member for dressing a wound according to claim 1, wherein the main body (10) comprises a stacked body composed of the protective layer (11), the pad layer (12), and a silicone pressure-sensitive adhesive layer (60).

5. The modified member for dressing a wound according to claim 4, wherein the pad layer (12) is obtained by impregnating a synthetic resin foam with hydrocolloid or hydrogel.

6. The modified member for dressing a wound according to claim 1, wherein the pad layer (12) is obtained by impregnating a synthetic resin foam with hydrocolloid or hydrogel.

\* \* \* \* \*